Figure 1:
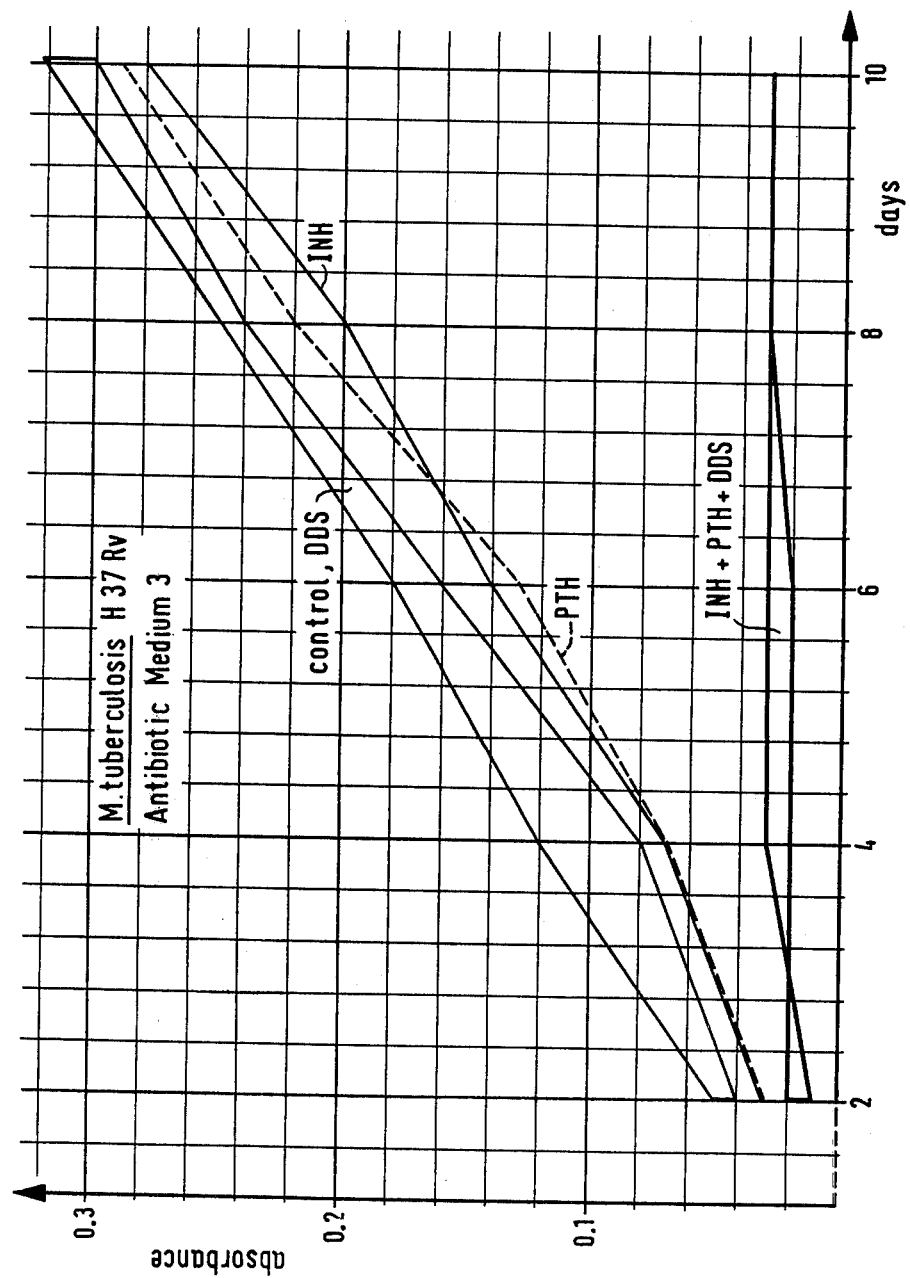

United States Patent [19]

Freerksen

[11] 4,005,207
[45] Jan. 25, 1977

[54] SYNERGISTIC THERAPEUTIC COMPOSITION FOR THE TREATMENT OF MYCOBACTERIOSES

[75] Inventor: Enno Freerksen, Borstel, Germany

[73] Assignee: Saarstickstoff-Fatol GmbH, Schiffweiler, Germany

[22] Filed: Aug. 7, 1974

[21] Appl. No.: 495,421

[30] Foreign Application Priority Data

Aug. 10, 1973 Germany ............................ 2340515

[52] U.S. Cl. ................................ 424/263; 424/266; 424/330
[51] Int. Cl.$^2$ .......................................... A61K 31/44
[58] Field of Search ................... 424/330, 266, 263

[56] References Cited

OTHER PUBLICATIONS

The Merck Index, 8th ed., Merck & Co., Inc., 1968, pp. 321, 586 and 879.
Freerksen et al., Arzweimittel–Forschowg 22, 1235–1242 (1972).

*Primary Examiner*—Jerome D. Goldberg
*Attorney, Agent, or Firm*—Brumbaugh, Graves, Donohue & Raymond

[57] ABSTRACT

The specification relates to an oral composition for the treatment of mycobacterioses, such as the treatment of leprosy and tuberculosis, containing an effective amount of isonicotinic acid hydrazide (international non-proprietary name isoniazid, designated herein as INH), an effective amount of 2-propyl-thioisonicotinic acid amide (prothionamide designated herein as PTH) and/or 2-ethyl-thioisonicotinic acid amide (ethionamide designated herein as ETH) and an effective amount of a sulfone and/or a sulfonamide with sustained activity. Suitable sulfones and sulfonamides with sustained activity, among others, are 4,4'-diaminodiphenyl-sulfone designated herein as DDS, sulfamethoxypyridazine and the like, as well as combinations of sulfones with sulfonamides, such as trimethoprimsulfonamides.

8 Claims, 10 Drawing Figures

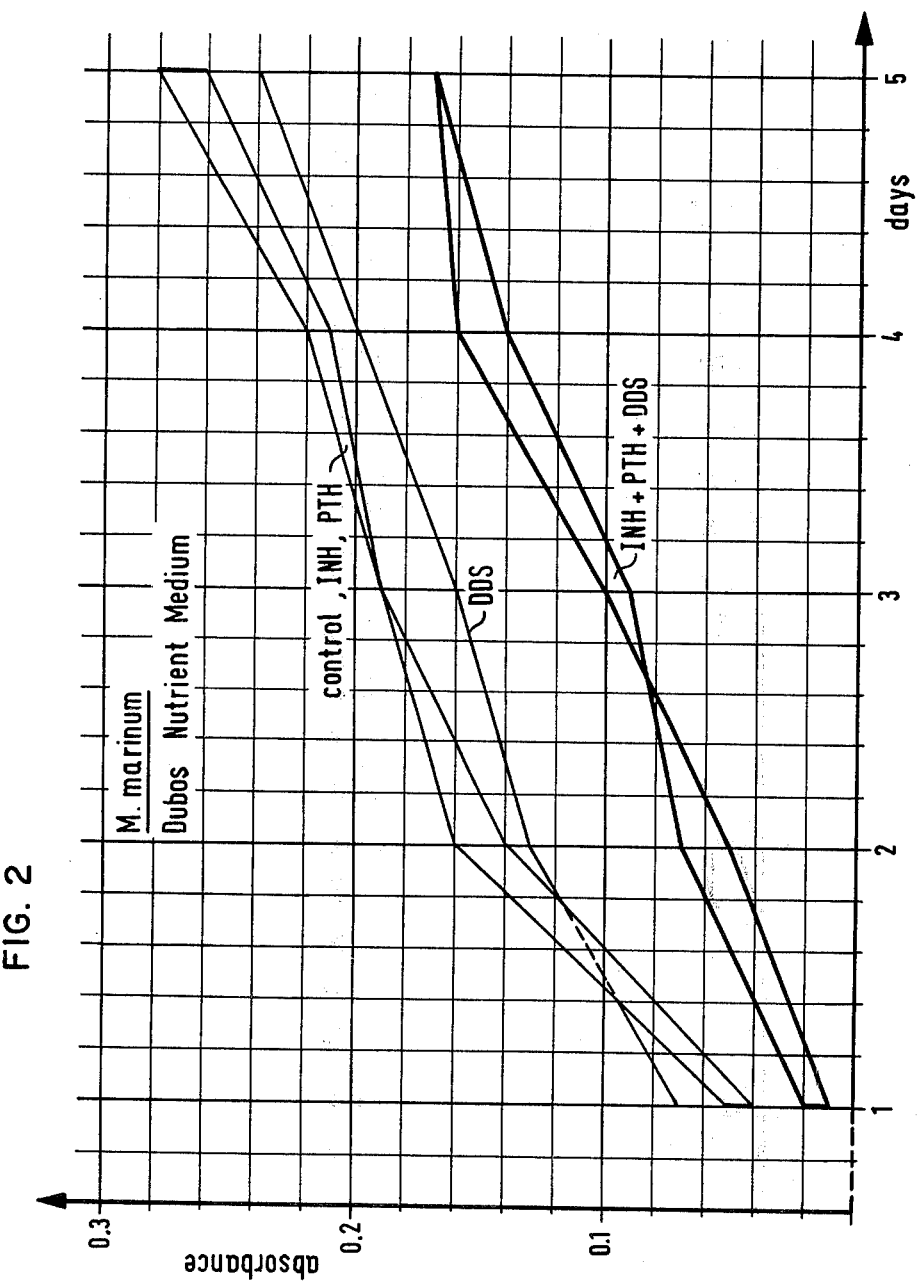

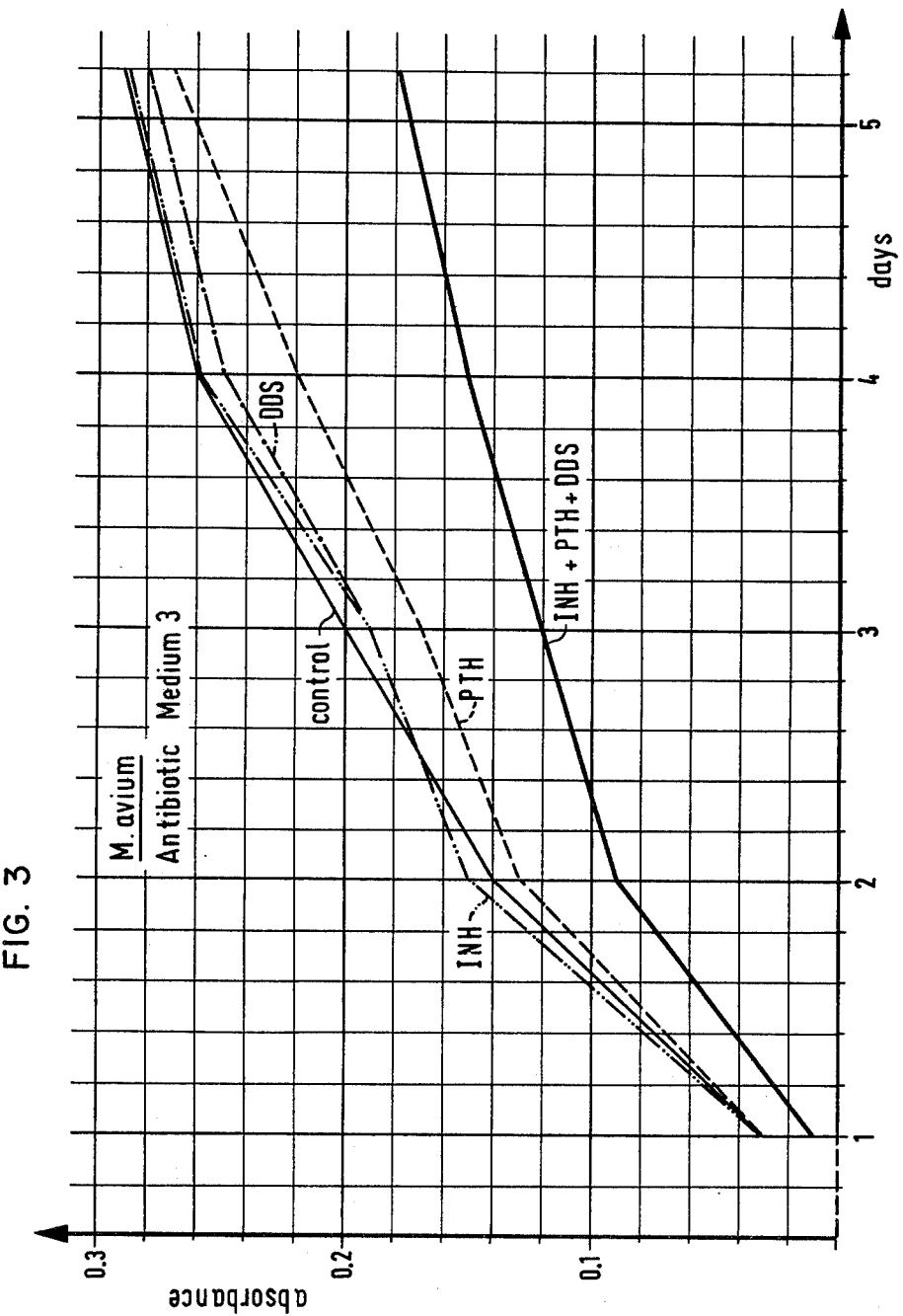

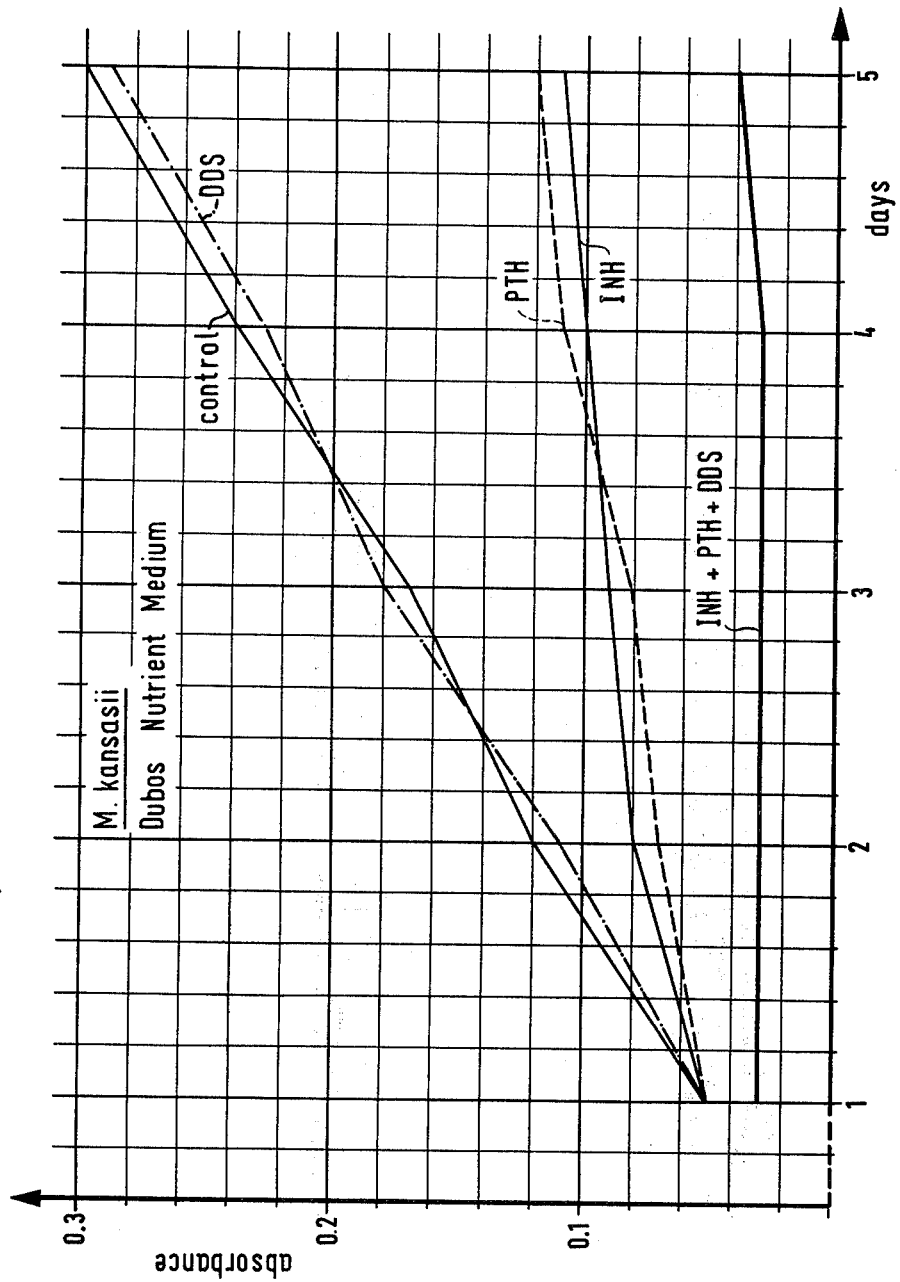

Fig. 5  Serum activity in man

Nutrient medium: Lockemann; Inoculation: 1 drop of $10^{-2}$; Serum dilution: $2^{-6}$ with addition of 4% serum

| PTH 5 mg/kg | h | 9th day $2^{-2}$ $2^{-3}$ $2^{-4}$ $2^{-5}$ $2^{-6}$ | 11th day $2^{-2}$ $2^{-3}$ $2^{-4}$ $2^{-5}$ $2^{-6}$ | 15th day $2^{-2}$ $2^{-3}$ $2^{-4}$ $2^{-5}$ $2^{-6}$ | 19th day $2^{-2}$ $2^{-3}$ $2^{-4}$ $2^{-5}$ $2^{-6}$ |
|---|---|---|---|---|---|
| M. tub. H₃₇ Rv | 0 | + + + + + | + + + + + | + + + + + | + + + + + |
| | 1 | (+) + + + + | + + + + + | + + + + + | + + + + + |
| | 3 | − (+) + + + | + + + + + | + + + + + | + + + + + |
| | 5 | (+) + + + + | + + + + + | + + + + + | + + + + + |
| | 7 | + + + + + | + + + + + | + + + + + | + + + + + |
| | 9 | (+) + + + + | + + + + + | + + + + + | + + + + + |
| | 24 | (+) + + + + | + + + + + | + + + + + | + + + + + |

| | h | 5th day | 7th day | 9th day | 15th day |
|---|---|---|---|---|---|
| M. kansasii RS 8316 | 0 | + + + + + | + + + + + | + + + + + | + + + + + |
| | 1 | − + + + + | − + + + + | + + + + + | + + + + + |
| | 3 | − − − + + | − − − + + | (+) + + + + | + + + + + |
| | 5 | − − − + + | − − + + + | − (+) + + + | + + + + + |
| | 7 | − − − + + | − − + + + | + + + + + | + + + + + |
| | 9 | (+) + + + + | (+) + + + + | + + + + + | + + + + + |
| | 24 | (+) + + + + | + + + + + | + + + + + | + + + + + |

| | h | 5th day | 6th day | 7th day | 12th day |
|---|---|---|---|---|---|
| M. marinum SN 1254 | 0 | + + + + + | + + + + + | + + + + + | + + + + + |
| | 1 | (+) + + + + | + + + + + | + + + + + | + + + + + |
| | 3 | − + + + + | − + + + + | − + + + + | + + + + + |
| | 5 | + + + + + | + + + + + | + + + + + | + + + + + |
| | 7 | + + + + + | + + + + + | + + + + + | + + + + + |
| | 9 | + + + + + | + + + + + | + + + + + | + + + + + |
| | 24 | + + + + + | + + + + + | + + + + + | + + + + + | one single dosage in the morning.

Fig. 6

Fig. 7a serum dilution

| M. marinum SN 1254 | h | 3rd day $\frac{1}{2^2}\frac{1}{2^3}\frac{1}{2^4}\frac{1}{2^5}\frac{1}{2^6}\frac{1}{2^7}$ | 6th day $\frac{1}{2^2}\frac{1}{2^3}\frac{1}{2^4}\frac{1}{2^5}\frac{1}{2^6}\frac{1}{2^7}$ | 10th day $\frac{1}{2^2}\frac{1}{2^3}\frac{1}{2^4}\frac{1}{2^5}\frac{1}{2^6}\frac{1}{2^7}$ | 13th day $\frac{1}{2^2}\frac{1}{2^3}\frac{1}{2^4}\frac{1}{2^5}\frac{1}{2^6}\frac{1}{2^7}$ |
|---|---|---|---|---|---|
| INH 5 mg/kg PTH 5 mg/kg | 0 | (+) (+) + + | + + + + | + + + + | + + + + |
| | 1 | − − − (+) + + | − − − + + + | − (+)(+) + + + | + + + + + + |
| | 3 | − − − + + + | − − + + + + | (+) + + + + + | + + + + + + |
| | 5 | − − + + + + | (+) + + + + + | + + + + + + | + + + + + + |
| | 7 | − (+) + + + + | + + + + + + | + + + + + + | + + + + + + |
| | 9 | − (+) + + + + | + + + + + + | + + + + + + | + + + + + + |
| | 24 | (+) + + + | + + + + | + + + + | + + + + |
| INH 5 mg/kg PTH 5 mg/kg DDS 2 mg/kg | 0 | (+) + + + | + + + + | + + + + | + + + + |
| | 1 | − − − − − + | − − − − + + | − − − (+) + + | (+) + + + + + |
| | 3 | − − − (+) + + | − − (+) + + + | − − + + + + | + + + + + + |
| | 5 | − − − + + + | + + + + + + | + + + + + + | + + + + + + |
| | 7 | − − (+) + + + | + + + + + + | + + + + + + | + + + + + + |
| | 9 | − − (+) + + + | + + + + + + | + + + + + + | + + + + + + |
| | 24 | − (+)(+) + | + + + + | + + + + | + + + + |
| INH 5 mg/kg PTH 5 mg/kg TSP 960 mg | 0 | (+) + + + | + + + + | + + + + | + + + + |
| | 1 | − − (+) + + + | − + + + + + | (+) + + + + + | + + + + + + |
| | 3 | − − − − + + | − (+) + + + + | − (+) + + + + | − + + + + + |
| | 5 | − − − (+) + + | − + + + + + | − + + + + + | − + + + + + |
| | 7 | − − − + + + | − (+) + + + + | − − + + + + | − + + + + + |
| | 9 | − − − + + + | − + + + + + | − + + + + + | − + + + + + |
| | 24 | − − (+) + | − (+) + + | + + + + | + + + + |
| RAMP 10 mg/kg INH 5 mg/kg PTH 5 mg/kg DDS 2 mg/kg | 0 | (+) + + + | + + + + | + + + + | + + + + |
| | 1 | − − − + + + | − + + + + + | + + + + + + | + + + + + + |
| | 3 | − − − − (+) + | − − − − + + | − − − − + + | − − (+) + + + |
| | 5 | − − − − − (+) | − − − + + + | − − − + + + | − − − + + + |
| | 7 | − − − − − (+) | − − (+) + + + | − − + + + + | − + + + + + |
| | 9 | − − − − (+) + | − − − + + + | − + + + + + | − + + + + + |
| | 24 | (+) + + + | + + + + | + + + + | + + + + | h = number of hours since bloodletting after having provided the drug once

Fig. 7b serum dilution

| M. marinum SN 1254 | h | 6th day | | | | | | | 11th day | | | | | | | 18th day | | | | | | |
|---|---|---|---|---|---|---|---|---|---|---|---|---|---|---|---|---|---|---|---|---|---|---|
| | | $2^{-2}$ | $2^{-3}$ | $2^{-4}$ | $2^{-5}$ | $2^{-6}$ | $2^{-7}$ | | $2^{-2}$ | $2^{-3}$ | $2^{-4}$ | $2^{-5}$ | $2^{-6}$ | $2^{-7}$ | | $2^{-2}$ | $2^{-3}$ | $2^{-4}$ | $2^{-5}$ | $2^{-6}$ | $2^{-7}$ | |
| RAMP 10 mg/kg | 0 | + | + | + | + | | | | + | + | + | + | | | | + | + | + | + | | | |
| | 1 | + | + | + | + | + | + | | + | + | + | + | + | + | | + | + | + | + | + | + | |
| | 3 | − | − | − | + | + | + | | − | − | + | + | + | + | | + | + | + | + | + | + | |
| | 5 | − | − | − | + | + | + | | − | (+) | + | + | + | + | | + | + | + | + | + | + | |
| | 7 | − | − | + | + | + | + | | + | + | + | + | + | + | | + | + | + | + | + | + | |
| | 9 | (+) | + | + | + | + | + | | + | + | + | + | + | + | | + | + | + | + | + | + | |
| | 24 | + | + | + | + | | | | + | + | + | + | | | | + | + | + | + | | | |
| RAMP 10 mg/kg PTH 5 mg/kg | 0 | + | + | + | + | | | | + | + | + | + | | | | + | + | + | + | | | |
| | 1 | − | − | − | + | + | + | | − | (+) | + | + | + | + | | + | + | + | + | + | + | |
| | 3 | − | − | − | − | + | + | | − | − | − | + | + | + | | − | − | (+) | + | + | + | |
| | 5 | − | − | − | + | + | + | | − | − | + | + | + | + | | − | + | + | + | + | + | |
| | 7 | − | − | (+) | + | + | + | | − | + | + | + | + | + | | + | + | + | + | + | + | |
| | 9 | − | − | + | + | + | + | | − | + | + | + | + | + | | + | + | + | + | + | + | |
| | 24 | + | + | + | + | | | | + | + | + | + | | | | + | + | + | + | | | |
| RAMP 10 mg/kg PTH 5 mg/kg INH 5 mg/kg | 0 | + | + | + | + | | | | + | + | + | + | | | | + | + | + | + | | | |
| | 1 | + | + | + | + | + | + | | + | + | + | + | + | + | | + | + | + | + | + | + | |
| | 3 | − | − | − | − | + | + | | − | − | − | + | + | + | | (+) | + | + | + | + | + | |
| | 5 | − | − | − | − | + | + | | − | − | − | (+) | + | + | | − | − | + | + | + | + | |
| | 7 | − | − | − | − | + | + | | − | − | (+) | + | + | + | | − | + | + | + | + | + | |
| | 9 | − | − | − | + | + | + | | − | − | + | + | + | + | | − | + | + | + | + | + | |
| | 24 | + | + | + | + | | | | + | + | + | + | | | | + | + | + | + | | | |
| RAMP 10 mg/kg PTH 5 mg/kg INH 5 mg/kg DDS 2 mg/kg | 0 | + | + | + | + | | | | + | + | + | + | | | | + | + | + | + | | | |
| | 1 | − | − | − | (+) | + | + | | − | − | (+) | + | + | + | | (+) | + | + | + | + | + | |
| | 3 | − | − | − | − | + | + | | − | − | − | (+) | + | + | | − | − | (+) | + | + | + | |
| | 5 | − | − | − | − | + | + | | − | − | − | + | + | + | | − | − | (+) | + | + | + | |
| | 7 | − | − | − | + | + | + | | − | − | (+) | + | + | + | | − | − | + | + | + | + | |
| | 9 | − | − | (+) | + | + | + | | − | + | + | + | + | + | | − | + | + | + | + | + | |
| | 24 | + | + | + | + | | | | + | + | + | + | | | | + | + | + | + | | | | h = number of hours since bloodletting after having provided the drug once

Fig. 8

Serum activity in man

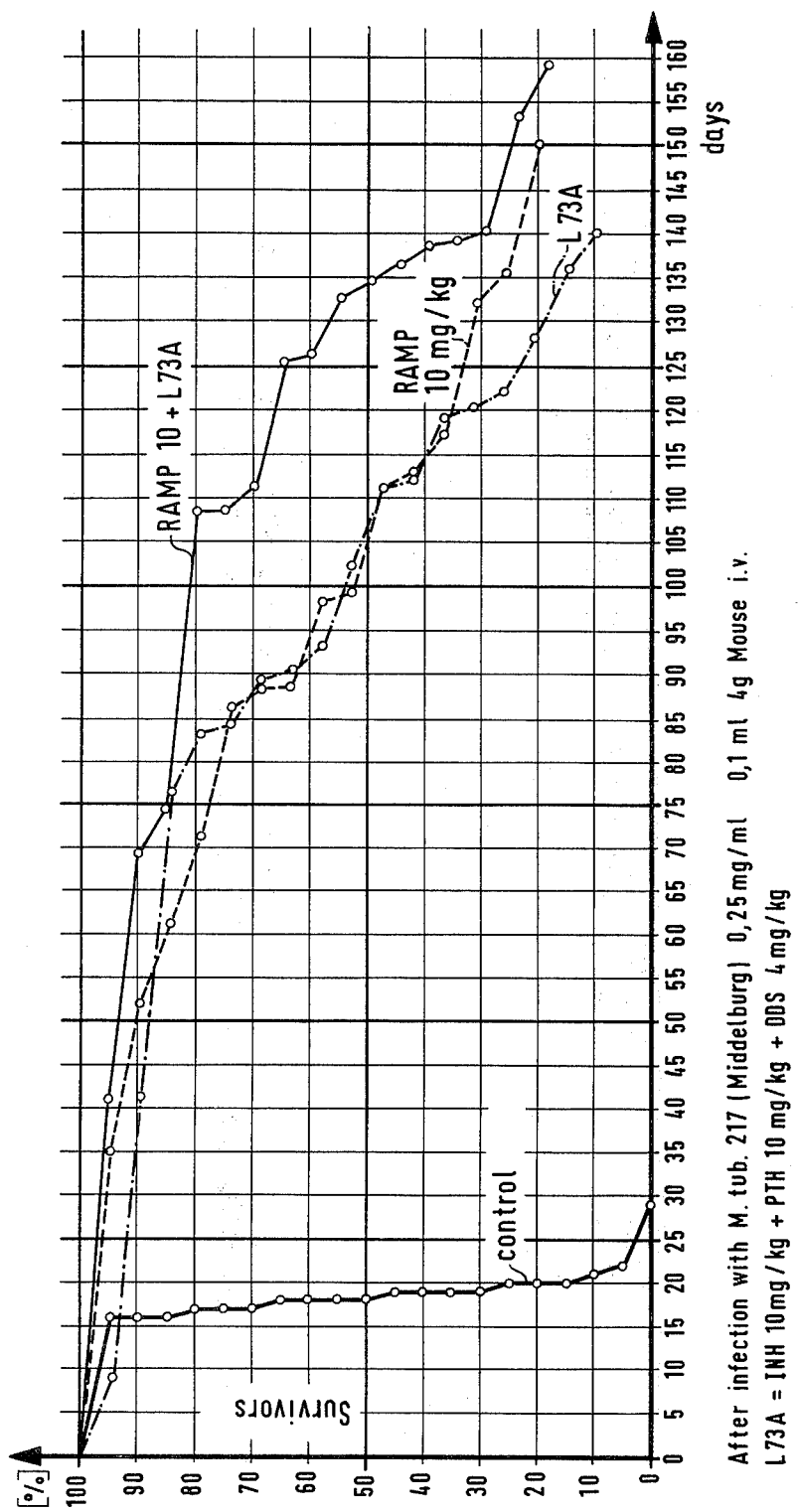

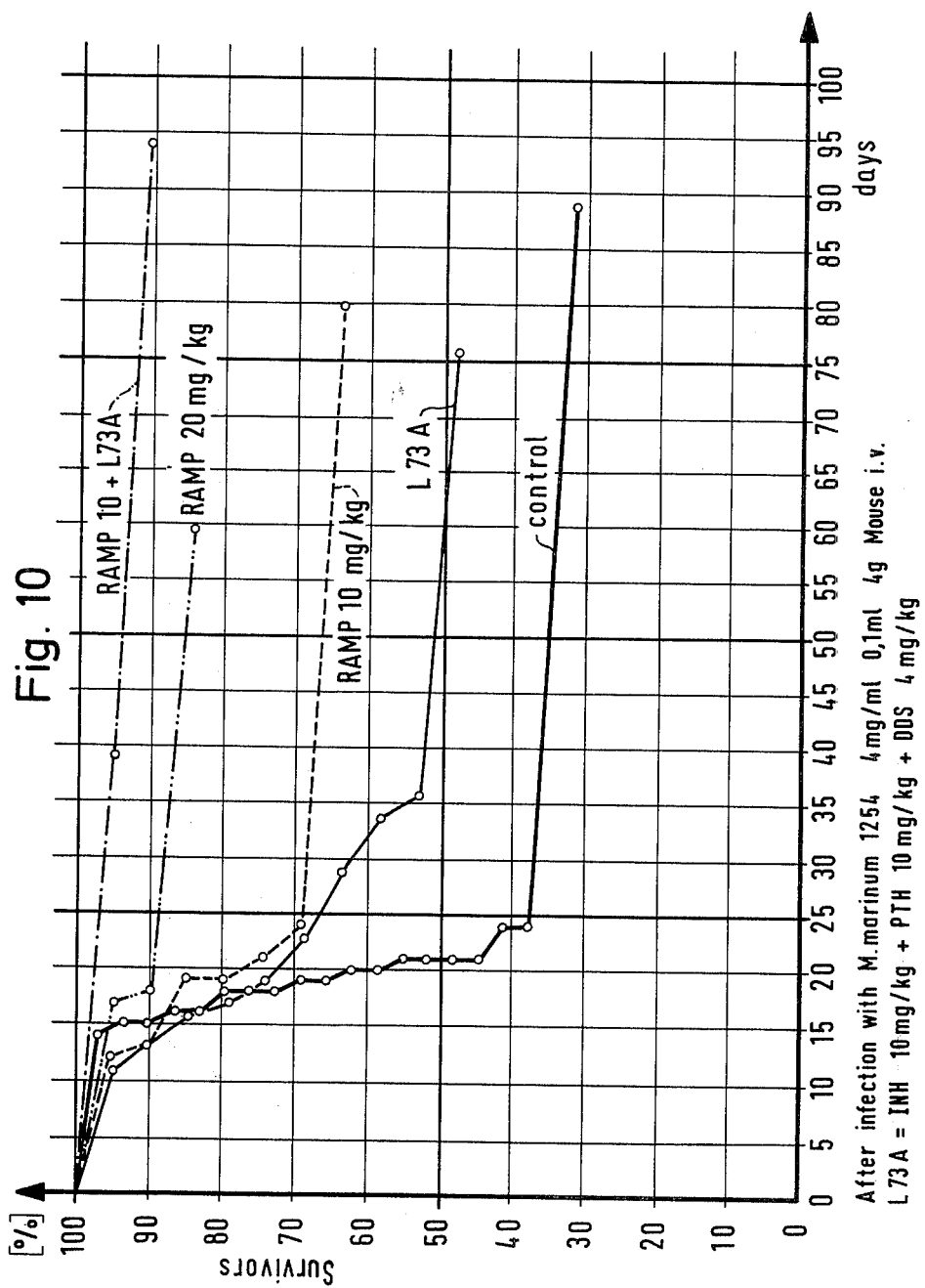

SYNERGISTIC THERAPEUTIC COMPOSITION FOR THE TREATMENT OF MYCOBACTERIOSES

BACKGROUND OF THE INVENTION

It is known that INH, ETH and PTH independently inhibit the growth of mycobacterium tuberculosis, which causes tuberculosis and, therefore, are successfully applied in the treatment of tuberculosis. However, each aforementioned compound virtually does not possess activity against mycobacterium leprae, which causes leprosy. The results obtained with INH in previous experiments with patients suffering from leprosy were disappointing; therefore, these tests were discontinued. Since experiments with ETH and PTH on patients with leprosy or favorable results obtained in such experiments have not been known, it has been concluded heretofore that these compounds also are not active against leprosy.

On the other hand, it is known that DDS possesses activity against the mycobacterium leprae and, therefore, it has been used for the treatment of leprosy. However, its use requires a lifelong treatment and has only an inhibitory effect. In addition, a resistance to the bacteria may result and a cure for leprosy is still not achieved.

Accordingly, it would be advantageous to have an improved composition for the treatment of leprosy and the like.

SUMMARY OF THE INVENTION

A synergistic composition has now been provided. Thus in accordance with this invention, it has now been found that a combination of the compounds INH, ETH and/or PTH, and DDS improves the inhibitory effect on the growth of mycobacterium leprae and, thus, enables a more effective therapy of the disease caused by this mycobacterium. Although the composition of the invention hereinafter is described as containing DDS, it is understood that other sulfones and/or sulfonamides can be used.

One advantage of the composition of the invention resides in the fact that the compounds used in the preparation thereof are easily available and low in cost. In cases of imcompatibility of rifampicin, which recently has been used for the treatment of tuberculosis and leprosy, moreover, the rifampicin can be replaced by the composition of the invention. In addition, it is possible to discontinue the treatment with rifampicin after a definite period of time and to continue the treatment with the composition of the invention, which is easier to obtain and less expensive. This is especially important for developing countries where leprosy occurs most frequently.

DESCRIPTION OF THE INVENTION

The dosage of INH in the composition of the invention is about 5 to 10 mg per kg body weight and this is within the range in which this compound has been used for the treatment of tuberculosis. The dosage of DDS is about 1 to 2 mg per kg body weight which is the range customarily used heretofore. With the composition of the invention, the duration of the treatment can be shortened. The sulfones and/or sulfonamides are defined in this invention as those compounds with sustained activity against mycobacterium disclosed in Erhart/Ruschig, Arzneimittel, Entwicklung, Wirkung, Darstellung, Vol. 4, Chemotherapeutika Part 1, 1972, page 86 seq. and page 145 seq., especially page 156, Verlag Chemie. A suitable sulfone is 4,4'-diaminodiphenyl-sulfone, a suitable sulfonamide is sulfamethoxypyridazine or a trimethoprim-sulfonamide combination, such as trimethoprim-sulfamethoxazol designated herein as TSP. In the composition of the invention, the dosage of PTH or ETH is about 5 to 10 mg per kg body weight. This is lower than the amount previously used in tuberculosis therapy, i.e., about 13 to 18 mg per kg body weight per day. By having this relatively low dosage, the compatibility of the PTH is improved. In addition, it has been surprisingly found that INH and ETH as well as PTH not only enhance the activity of DDS against leprosy in a synergistic manner, but that DDS, which is virtually inactive against tuberculosis, potentiates the activity of tuberculostatics when applied simultaneously with these other compounds. Here too, a synergistic effect is provided which enables either the achievement of a better therapeutic activity with the same amount of tuberculostatics as heretofore, or the same degree of therapeutical activity with a substantially lower amount of tuberculostatics.

Certain optional active ingredients can be used with the composition of the invention, such as rifampicin (designated herein as RAMP), ethambutol (designated herein as EMB and streptomycin (designated herein as SM). Well known inert carriers and auxiliary agents can be included, if desired. Suitable carriers, among others, are carbowaxes (solid polyethylene glycols) and polyvinylpyrrolidones. Suitable disintegrating agents, among others, are formalin-casein and starch. As lubricant, among others, magnesium stearate can be used. The carriers and/or auxiliary agents are used in an amount of about 1 – 2 mg/kg of body weight. A composition with rifampicin is suitable until germ-freeness is reached. The administration of the expensive rifampicin can then be discontinued, and the therapy can proceed without it.

The therapeutic effect can be accomplished by administering separately each component of the composition of the invention. For the sake of convenience and in order to avoid failures in the dosages, it is preferred to combine them in one preparation.

The composition of the invention can be manufactured in the form of tablets, e.g., dragees and for special indications as preparations for injections and infusions. It is also possible to use it in capsules. Partitioned capsules are appropriate when the individual components should not come into contact with each other prior to administration. This provides for a simple therapy for controlling epidemics and for a consistent anti-bacterial treatment.

The combination of tuberculostatics with DDS according to the invention is different from the combinations made from other tuberculostatics which have been employed in the treatment of tuberculosis (INH + p-aminosalicyclic acid + streptomycin, rifampicin + 2,2'-ethylenediimino-di-1-butanol + INH or INH+ PTH + p-aminosalicyclic acid, etc.). With these prior combinations of three compounds, each of which is tuberculostatically active, the primary resistant parts of pathogenic bacteria populations are to be combatted due to the different mechanism of the active ingredients. However, with the combination of the invention having DDS (which is virtually inactive against tuberculosis) and PTH (which is virtually inactive against tuberculosis in the used dose) the tuberculostatic activity is synergistically increased. Due to the low dosage of the single ingredients which are used in the composition of the invention, the side effects are extremely low. It is surprising, moreover, that the high activity of the composition of the invention is achieved with amounts of the single ingredients that are below the dosages which are necessary for a monotherapy.

In the periodical "Der Internist", Volume 14, pages 100 et seq. (1973) "Zum gegenwartigen Stand der antituberkulosen Chemotherapie" by K. L. Radenbach, it is stated (sub item 3) that a successful combination therapy of the tuberculosis requires that each single active agent be applied in a single and daily dosis of safe antibacterial activity, that clinically inactive or barely active substances are unsatisfactory and that solid combined preparations are not suitable if they contain the active dose of a medicinal and the inactive dose of another component. In a combination therapy, no additive and much less a potentiating effect of the anti-tuberculosis agents is occurring, and the combination therapy solely serves the prevention of a secondary resistance by selection of less primary resistant mutants which are existent within each population of sensitive tubercle bacteria. However, in the invention the combination of INH + ETH or PTH + DDS with or without rifampicin, in amounts which are below the doses of the single active ingredients for possessing full anti-bacterial activity, produces a synergistic increase in activity and results in a composition which simultaneously is active against tuberculosis and leprosy and in addition combats diseases which are caused by in-vitro reproducible atypical mycobacteria, e.g. Buruli-ulcus. Up to now the latter disease which occurs in tropical regions and which is caused by mycobacterium ulcerans, has been rather resistant against medical therapy. The above-stated composition is furthermore active against mycobacterium kansasii, mycobacterium fortuitum and mycobacterium avium. All these microorganisms may cause diseases also in European regions.

The combination of a synergistically increased activity against leprosy, a synergistically increased anti-tuberculous activity and simultaneous activity against atypical mycobacterioses is of extreme importance not only by itself but because frequently a patient suffers from several mycobacterioses, for example from leprosy and tuberculosis. The composition of the invention, which shows a broad spectrum of activity against mycobacterioses, is mainly administered orally. It facilitates the control of epidemics from an economical and organizational point of view in an extraordinary manner. Complicated diagnostical experiments, sensitivity tests and the determination of the resistance, which otherwise are indispensible for a systematic therapy, may no longer be necessary in most cases. The term "mycobacterioses" is defined herein as any disease which can be controlled and/or cured by the administration of the composition of the invention.

The following examples are submitted to illustrate but not to limit this invention. Unless otherwise indicated, all parts and percentages in the specification and claims are based upon weight.

EXAMPLES 1 – 10

Although mycobacterium leprae can not be cultivated in the laboratory, it has been ascertained that for in-vitro tests mycobacterium marinum and some other so-called atypical mycobacteria can be substituted for mycobacterium leprae (see Enno Freerksen and Magdalena Rosenfeld, Arzneimittel-Forschung 22, 1235 – 1242 (1972) "A New Analogous Model for the Detection and Evaluation of Chemotherapeutic Products Effective in Leprosy"). For the former mycobacterium and others, in-vitro tests as well as animal tests were conducted. The results of the in-vitro tests are summarized in FIGS. 1 to 8. FIGS. 5 to 8 show the inhibitory serum activity in man after the application of a single dose/day of the drug(s). The tuberculostatics were applied to the test persons singly or in combination. Prior to the application of the drugs and thereafter examples of the blood were taken from the test persons. The samples were centrifuged. Then the serum was recovered under sterile conditions. The thus obtained serum was diluted with 4 or 6% bovine serum, respectively, in the ratio 1:10, 1:100, 1:1000 etc. and admixed to the liquid nutrient medium according to Lockemann (asparagine 5,0 g; $NaH_2PO_4$ 3,0 g; Na-citrate 2,5 g; $KH_2PO_4$ 4,0 g; $MgSO_4$ 2,5 g; ferric ammonium sulfate 0,01 g; glycerine 25,0 ml; dist. water ad 1000 ml; bovine serum 4%). Subsequently the tubes were inoculated with the indicated mycobacterium strain and incubated at 37°C. In the tubes containing serum of a sufficient concentration of the administered drug(s) the growth of the mycobacteria was inhibited for a shorter or longer period of time ("−" in FIGS. 5 to 8). Where the concentration of the tuberculostatic(s) was not sufficient the bacterial growth was inhibited to a more or less degree (" (+)", "+", "++" up to "+++" in FIGS. 5 to 8). The results of the in-vitro tests are confirmed by animal tests (FIGS. 9 and 10) and by the results obtained with a statistically relevant number of clinical and ambulant patients. In the animal tests white mice were infected i.v. with M. tuberculosis Middelburg (0,25 mg/ml; 0,1 ml/4g mouse, i.v.) or with M. marinum 1254 (4 mg/ml; 0,1 ml/4g mouse i.v.). About 7 days later the mice were treated with a daily dosage of L 73 A (INH 10 mg/kg + PTH 10 mg/kg + DDS 4 mg/kg), 10 mg/kg RAMP, 20 mg/kg RAMP and 10 mg/kg RAMP + L 73 A, respectively, for about 3 weeks. FIGS. 1 to 10 correspond to Examples 1 to 10, respectively.

Referring to FIGS. 1 to 4, for Examples 1 to 4, definite concentrations of the chemotherapeutical agents, INH, PTH and DDS, were added to liquid nutrient media. The used concentrations were below the minimum inhibitory concentrations as known in the art. They were as follows:

| Figure 1 | | | |
|---|---|---|---|
| INH | $1 \times 10^{-7}$ M | = | 0.0137 mcg/ml |
| PTH | $1 \times 10^{-6}$ M | = | 0.018 mcg/ml |
| DDS | $1 \times 10^{-4}$ M | = | 25 mcg/ml |
| Figure 2 | | | |
| INH | $1 \times 10^{-5}$ M/ml | | |
| PTH | $1 \times 10^{-6}$ M/ml | | |
| DDS | $1 \times 10^{-6}$ M/ml | | |
| Figure 3 | | | |
| INH | $1 \times 10^{-5}$ M | | |
| PTH | $1 \times 10^{-5}$ M | | |
| DDS | $1 \times 10^{-4}$ M | | |
| Figure 4 | | | |
| INH | $1 \times 10^{-6}$ M | | |
| PTH | $5 \times 10^{-6}$ M | | |
| DDS | $1 \times 10^{-4}$ M | | |

The individual nutrient media were inoculated with suspensions of the mycobacteria and incubated at 37° C. The turbidity of the culture media was measured during the period of 10 days at the wave length 520 nm (absorption 0.1; 0.2; 0.3, etc.) by means of a spectrophotometer (Bausch and Lomb Spectronic 20).

The antibiotic medium 3 (Difco) had the following composition:

| | |
|---|---|
| Bacto meat extract | 1.5 g |
| Bacto yeast extract | 1.5 g |
| Bacto peptone | 5 g |
| Bacto glucose | 1 g |
| NaCl | 3.5 g |
| $K_2HPO_4$ | 3.68 g |
| $KH_2PO_4$ | 1.32 g | in 1000 ml distilled water + 0.05% Tween 80 (Serva) + 2g Na-glutaminate (Merck).

The liquid nutrient medium Dubos (Merck) was composed of the following:

| | |
|---|---|
| Yeast extract | 2.0 g |
| Special peptone | 4.0 g |
| Na-citrate | 1.5 g |
| $MgSO_4$ | 0.6 g |
| $Na_2HPO_4$ | 2.5 g |
| $KH_2PO_4$ | 1.0 g | in 1000 ml distilled water + 0.05% Tween 80 (Serva) + 2g Na-glutaminate (Merck).

FIG. 1 shows that the combination of the active ingredients DDS, INH and PTH in concentrations, each alone of which does not inhibit the growth of *M. tuberculosis* H 37 Rv, achieves complete inhibition.

FIG. 2 demonstrates that the anti-tuberculous agents INH and PTH, which are inactive against *M. marinum*, increase the activity of the leprosis-controlling DDS.

According to FIG. 3, the combination of INH + PTH + DDS inhibits the growth of the extremely resistant atypical *M. avium*.

As evident from FIG. 4, the combination of INH + PTH + DDS inhibits the growth of *M. kansasii* markedly.

Examples 5 to 8, FIGS. 5 to 8, respectively, relate to serum activity determinations in man. FIG. 5 shows the inhibitory serum activity of PTH against *M. tuberculosis* H 37 Rv, *M. kansasii* and *M. marinum*, after administration of a single dosage. The inhibitory serum activity is recorded after four different periods of time. The later the serum activity is determined – provided there is no bacterial growth — the more it can be assumed that the serum concentration of the applied drugs was sufficient or sufficiently synergistic to assure a bactericidal or at least a long-lasting bacteriostatic effect. It was to be expected that after the application of 5 mg/kg PTH the serum activity with *M. tuberculosis* H 37 Rv is very low. However, this does not prove to be the case with the atypical strain *M. kansasii* and even some activity is noticed with *M. marinum*.

Figure 6:
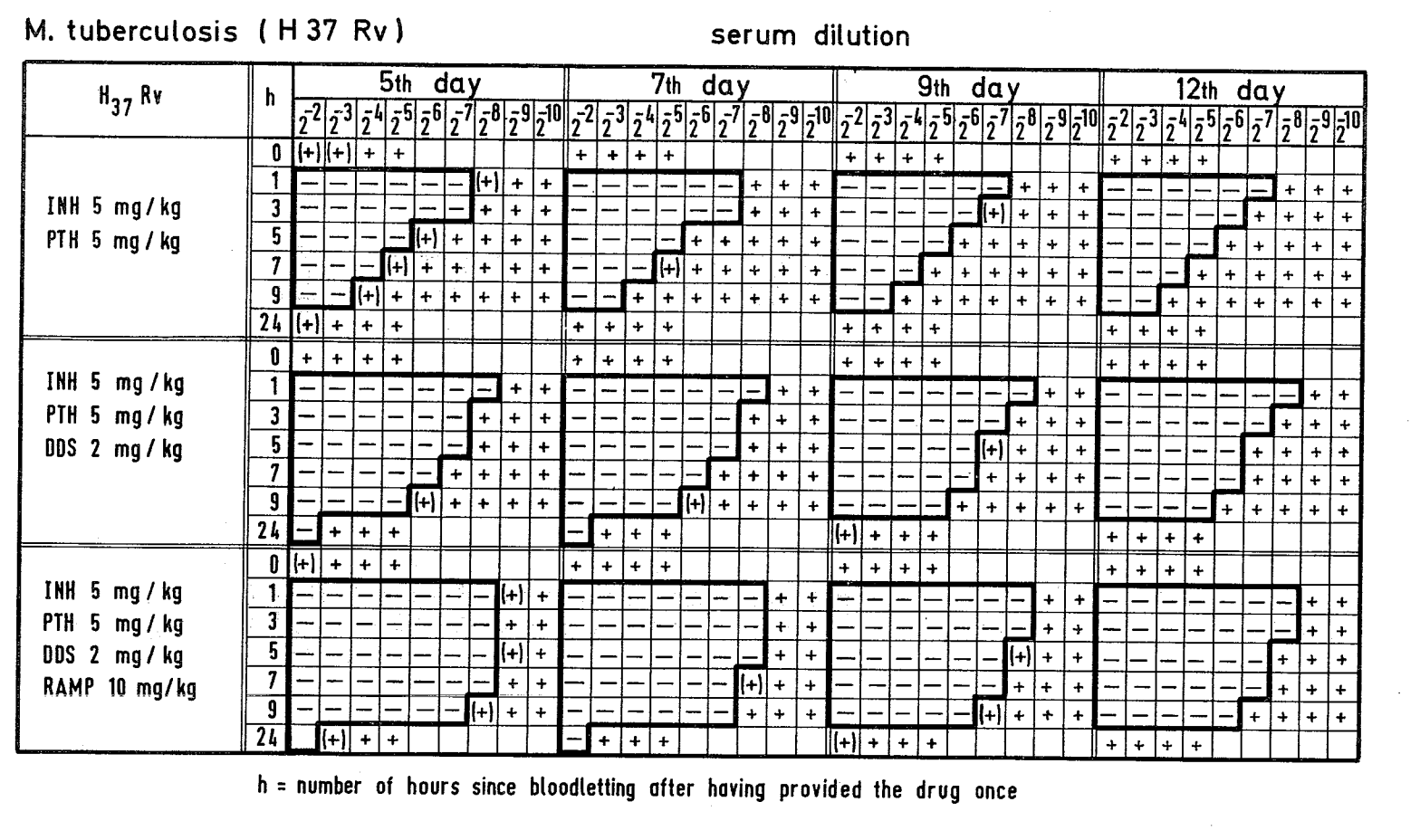

Referring to FIG. 6, the combined use of PTH and INH produces an essential enhancement of the serum activity with respect to the dilution and to the time after the application, which is furthermore enhanced by the simultaneous application of DDS, which compound has no inhibitory activity in-vitro against *M. tuberculosis*. The achieved effect is even better when RAMP (rifampicin) is also applied.

FIGS. 7a and b indicate that the activity of INH and PTH against *M. marinum* is enhanced by the simultaneous administration of DDS and a further increase in activity is reached if additionally RAMP is applied.

Figure 8:
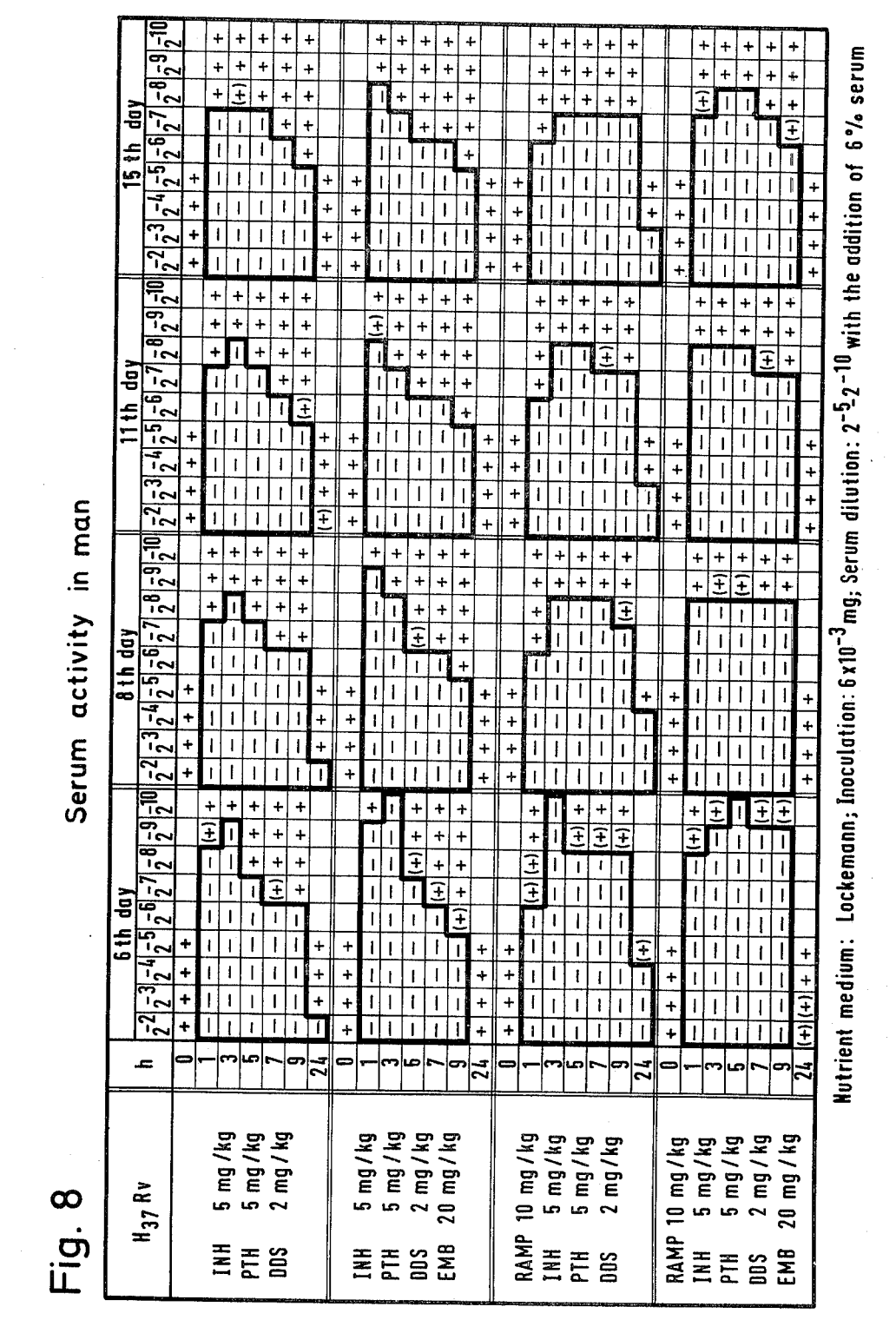

As shown in FIG. 8, the combination INH + PTH + DDS has a remarkable activity against *M. tuberculosis* H 37 Rv which can be further increased by RAMP or EMB (ethambutol). A further increase in activity can be reached by the addition of both RAMP and EMB.

From FIG. 9, the high activity of the combination INH + PTH + DDS against *M. tuberculosis* is evident. This can be increased further by the addition of RAMP.

Fig. 10 shows that the combination INH + PTH + DDS is also active against *M. marinum* and produces high activity in combination with RAMP.

With further reference to Examples 1 to 10 (FIGS. 1 to 10), treatment with DDS usually requires a lifelong treatment and in many cases even a treatment lasting for decades does not result in a bacterial negativation (disappearance of bacteria from sputum, tissues, urine, liquor, pus, etc.). Such a bacterial negativation is reached in up to 90% of the treated patients within a period of time of 18 months when the composition of the invention is applied together with rifampicin. Thus, the combination INH, ETH and/or PTH with DDS produces a surprising synergistic enhancement of activity.

Example 11

A dragee can be prepared from the following ingredients:
83 mg INH
84 mg PTH
33 mg DDS With formalin-casein, carbowax and polyvinylpyrrolidone as carriers and auxiliary agents the total weight of the dragee was brought to 375 mg. The thus obtained dragee was coated with an Eudragit E (Rohm + Haas GmbH, Darmstadt) lacquer.

Example 12

A tablet was prepared from:
175 mg INH
175 mg PTH
50 mg DDS
30 mg formalin-casein
16 mg carbowax
4 mg polyvinylpyrrolidone The INH, PTH, DDS, formalin-casein and polyvinylpyrrolidone were granulated by an ethanolic solution of the carbowax and after the evaporation of the ethanol pressed into a tablet.

The tablet thus prepared was provided with an Eudragit E lacquer-coating.

Having set forth the general nature and specific embodiments of the present invention, the true scope is now particularly pointed out in the appended claims.

What is claimed is:
1. A synergistic therapeutic composition for the treatment of mycobacterioses in mammals comprising about 83 mg isonicotinic acid hydrazide, about 84 mg 2-propyl-thioisonicotinic acid amide, and about 33 mg 4,4'-diaminodiphenyl-sulfone per dosage unit.

2. A synergistic therapeutic composition for the treatment of mycobacterioses in mammals comprising about 175 mg isonicotinic acid hydrazide, about 175 mg 2-propyl-thioisonicotinic acid amide, and about 50 mg 4,4'-diaminodiphenyl-sulfone per dosage unit.

3. A synergistic therapeutic composition for the treatment of mycobacterioses in mammals comprising about 5 to 10 mg isonicotinic acid hydrazide, about 5 to 10 mg 2-propyl-thioisonicotinic acid amide, and about 1 to 2 mg 4,4'-diaminodiphenyl-sulfone per kilogram of body weight.

4. The composition according to claim 3 comprising about 5 mg isonicotinic acid hydrazide, about 5 mg 2-propyl-thioisonicotinic acid amide and about 2 mg 4,4'-diaminodiphenyl sulfone per kilogram of body weight.

5. A process for treating mycobacterioses in mammals which comprises administering orally to mammals having mycobacterial diseases a synergistic composition comprising about 83 mg isonicotinic acid hydrazide, about 84 mg 2-propyl-thioisonicotinic acid amide, and about 33 mg 4,4'-diaminodiphenyl-sulfone per dosage unit.

6. A process for treating mycobacterioses in mammals which comprises administering orally to mammals having mycobacterial diseases a synergistic composition comprising about 175 mg isonicotinic acid hydrazide, about 175 mg 2-propyl-thioisonicotinic acid amide, and about 50 mg 4,4'-diaminodiphenyl-sulfone per dosage unit.

7. A process for treating mycobacterioses in mammals which comprises administering orally to mammals having mycobacterial diseases a synergistic composition comprising about 5 to 10 mg isonicotinic acid hydrazide, about 5 to 10 mg 2-propyl-thioisonicotinic acid amide, and about 1 to 2 mg 4,4'-diaminodiphenyl-sulfone per kilogram of body weight.

8. A process according to claim 7 in which the synergistic composition comprises about 5 mg isonicotinic acid hydrazide, about 5 mg 2-propyl-thioisonicotinic acid amide, and about 2 mg 4,4'-diaminodiphenyl sulfone per kilogram of body weight.

* * * * *